United States Patent
Mahrenholtz et al.

(10) Patent No.: US 7,662,634 B2
(45) Date of Patent: Feb. 16, 2010

(54) METHOD AND DEVICE FOR DETERMINING THE ISOMER COMPOSITION IN ISOCYANATE PRODUCTION PROCESSES

(75) Inventors: Jochen Mahrenholtz, Krefeld (DE); Andrea Wimschneider, Düsseldorf (DE); Hans-Georg Pirkl, Leverkusen (DE); Heinz-Herbert Müller, Krefeld (DE); Stefan Dresely, Krefeld (DE); Jeffrey Bolton, Baytown, TX (US); Martin Schiffhauer, Erkrath (DE); Udo Wolf, Kempen (DE); Johannes Schweer, Köln (DE); Martin Gerlach, Dormagen (DE)

(73) Assignee: Bayer MaterialScience AG, Leverkusen (DE)

(*) Notice: Subject to any disclaimer, the term of this patent is extended or adjusted under 35 U.S.C. 154(b) by 798 days.

(21) Appl. No.: 10/845,727

(22) Filed: May 14, 2004

(65) Prior Publication Data
US 2005/0003553 A1    Jan. 6, 2005

(30) Foreign Application Priority Data
May 19, 2003    (DE) .............................. 103 22 439

(51) Int. Cl.
*G01N 33/00* (2006.01)
(52) U.S. Cl. .................. 436/109; 436/55; 436/106; 422/62; 702/27
(58) Field of Classification Search .............. 702/27; 436/55, 109, 106; 422/62
See application file for complete search history.

(56) References Cited

U.S. PATENT DOCUMENTS

| | | | |
|---|---|---|---|
| 5,638,284 A | 6/1997 | Helmer et al. | 364/471.01 |
| 5,707,870 A | 1/1998 | Moessner | 436/55 |
| 5,712,481 A | 1/1998 | Welch et al. | 250/339.12 |
| 5,717,209 A | 2/1998 | Bigman et al. | 250/339.12 |
| 5,808,131 A * | 9/1998 | Gruenbauer et al. | 560/25 |
| 6,072,576 A | 6/2000 | McDonald et al. | 356/300 |
| 6,103,934 A | 8/2000 | Hallinan et al. | 562/517 |
| 6,162,644 A * | 12/2000 | Choi et al. | 436/55 |
| 6,228,650 B1 | 5/2001 | Moore et al. | 436/55 |
| 6,294,764 B1 | 9/2001 | Lindner et al. | 219/494 |
| 6,300,633 B1 | 10/2001 | Hunt et al. | 250/339.12 |
| 6,339,222 B1 | 1/2002 | Kester et al. | 250/339.09 |
| 6,362,366 B1 | 3/2002 | Hallinan et al. | 562/517 |
| 6,552,221 B1 | 4/2003 | Hallinan et al. | 562/519 |
| 2003/0228355 A1 | 12/2003 | Zarif et al. | 424/450 |

FOREIGN PATENT DOCUMENTS

| | | |
|---|---|---|
| DE | 2 139 269 | 2/1973 |
| DE | 273 175 | 11/1989 |
| DE | 100 05 130 | 8/2001 |
| JP | 11-350368 | 12/1999 |
| JP | 2000-146835 | 5/2000 |
| JP | 2000-298512 | 10/2000 |
| WO | 00/68664 | 11/2000 |

OTHER PUBLICATIONS

Balfour et al, The Infrared and Raman spectra of methoxycarbonyl and thiomethoxycarbonyl isocyanates, Can. J. Chem. 71(10): 1627-1631 (1993).*

(Continued)

*Primary Examiner*—Lyle A Alexander
*Assistant Examiner*—Dennis M White
(74) *Attorney, Agent, or Firm*—Connolly Bove Lodge & Hutz LLP

(57) ABSTRACT

The invention relates to a method for determining the isomer composition in an isocyanate isomer mixture, wherein a spectrum of the isomer mixture is recorded and the spectrum is entered into a chemometric calibration model.

12 Claims, 8 Drawing Sheets

OTHER PUBLICATIONS

Kondyurin et al, Vibrational Spectra of some Diisocyanates in the Liquid State or on EPDM-40 Rubber Surface, J. Applied Polymer Sci. 54, 1385-1393 (1994).*

ISO/TR 9372: 1993, International Organization for Standardization: Abstract: Plastics—Basic materials of polyurethanes—Determination of the amounts of 2,4-and 2,6-isomers in toluenediisocyanate by infrared spectroscopy.*

Allport et al "MDI and TDI: Safety, Health and the Environment", Wiley, Mar. 28, 2003, pp. 302-303, 312, 324.*

J. Near Infrared Spectroscopy, 1, (month unavailable) 1993, pp. 221-245, Jerry Workman, Jr., "A review of process near infrared spectroscopy: 1980-1994".

Antec, (month unavailable) 1992, pp. 2674-2676, A. Khettry et al, "In-Line Near-Infrared Monitoring of Polymeric Processes".

J. Applied Polymer Science, vol. 84, (month unavailable) 2002, pp. 2670-2682, Raphael A. M. Vieira et al, "In-Line and In Situ Monitoring of Semi-Batch Emulsion Copolymerizations Using Near-Infrared Spectroscopy".

Talanta,50 (month unavailable) 1999, pp. 283-290, Thomas Rohe et al, "Near infrared (NIR) spectroscopy for in-line monitoring of polymer extrusion processes".

Journal of Chemometrics, 14, (month unavailable) 2000, pp. 513-528, Charles E. Miller "Chemometrics for on-line spectroscopy applications—theory and practice".

J. Chem Inf. Comput. Sci., 40, (month unavailable) 2000, pp. 1093-1100, Olusola O. Soyemi et al, "Multivariate Analysis of Near-Infrared Spectra Using the G-Programming Language", Also see the Supporting Information Attached.

* cited by examiner

METHOD AND DEVICE FOR DETERMINING THE ISOMER COMPOSITION IN ISOCYANATE PRODUCTION PROCESSES

BACKGROUND OF THE INVENTION

The present invention relates to a method of determining the isomer composition of an isocyanate isomer mixture during isocyanate production processes, and to a method for the regulation or control of an isocyanate isomer production system for mixing or separating isomers. This invention also relates to an apparatus for the production of an isomer mixture with a setpoint isomer composition.

From the prior art, it is known to produce an isomer mixture of isocyanates, with a particular isomer composition, by means of an isomer production system.

For example, isomer separation can be carried out by means of distillation or crystallisation. Alternatively, a particular isomer mixture may be produced by mixing suitable initial isomer mixtures. The quality of the isomer mixture, for example in distillative isomer separation, can be regulated roughly through the process parameters of pressure and temperature, as well as the distillate/bottom-product ratios and reflux ratios. A disadvantage of this, however, lies in that with high product purities, the pressure and temperature provide almost no useful information about the concentration of the isomers. In other words, the sensitivity of the concentration determination is on the order of the measurement noise since the boiling points are close together. Furthermore, no physical method is yet known to be suitable for the determination of isocyanate isomer mixtures.

Previously, therefore, this quality monitoring has been carried out by taking samples and by, for example, subsequent manual chromatographic analysis, preferably gas chromatography (GC), of these samples. In the case of isocyanates, it is necessary to take occupational safety and environmental protection conditions into account, in order to avoid risks involved in the handling of such chemical substances. Furthermore, the number of samples that can be realistically taken is limited due to the associated labor cost, and information about the composition of the sample is not available until after a significant delay. Thus, in order to control the product quality of crystallizers or distillation columns, this manual method has significant disadvantages. This is particularly a problem since it does not allow any persistent trend to be established with respect to the concentration changes in many equipment components of a complex system.

With manual controls and sampling, it is conceivable that the isomer mixture being produced may have a relatively large difference in isomer content from the setpoint composition, particularly over relatively long periods of time. This can result in a reduction of the product quality or the production of waste.

Process chromatography or automated titration are relevant online methods for analyzing or assessing the isomer composition of an isomer mixture. A feature common to these methods is that the result is only available with a significant time delay after lengthy measurement times. Furthermore, these methods are characterised by elaborate sample delivery means, susceptibility to interference, and sizable consumption of the auxiliary agents and other consumable materials.

Monitoring and regulation of the isomer composition is important, and particularly, for the production of isocyanates. In this context, various isocyanates A, B, C, D, etc. consist of a mixture of two or more isomers $1, 2, 3, \ldots, n$.

These isocyanates include, for example, be naphthylene diisocyanate (bis-[isocyanate]naphthylene), xylylene diisocyanate (bis-[isocyanatomethyl]benzene), methylene diphenyl diisocyanate (MDI) or toluene diisocyanate (TDI), as well as other aromatic, alicyclic or aliphatic isocyanates, and mixtures thereof. In general, isocyanate intermediate or commercial products consist of the various isomers in different ratios.

Industrially, such isocyanate intermediate or commercial products are produced from an initial isocyanate mixture (i.e. a raw mixture) of a plurality of isomers $1, 2, 3, \ldots, n$.

For example, isocyanate A may be toluene diisocyanate (TDI), an isomeric mixture of the isomers 2,4-TDI (2,4-bis-[isocyanate]benzene), 2,6-TDI (2,6-bis-[isocyanate]benzene), 2,3-TDI and 3,4-TDI. The initial mixture may be separated into its isomers in order to achieve special high-quality product properties. For instance, the initial mixture may be separated into a commercial product I with 100% 2,4-TDI, and/or a commercial product II with about 65% 2,4-TDI and about 35% 2,6-TDI. Commericaly products such as these are available on the market. Another example is isocyanate B, which may be methylene diphenyl diisocyanate (MDI), an isomeric mixture of the isomers 2,2'-MDI (bis-[2-isocyanatophenyl]methane), 2,4'-MDI (2-isocyanatophenyl)-(4-isocyanatophenyl)methane, 4,4'-MDI (bis-[4-isocyanatophenyl]methane) and other isomers with a higher ring number (i.e. more than 2 ring compounds).

The initial isocyanate mixture may be separated into its isomers in order to achieve special high-quality product properties. For instance, a commercial product I with 100% 4,4'-MDI and a commercial product II with about 50% 2,4'-MDI and about 50% 4,4'-MDI, both of which are available on the market.

It is absolutely necessary that the monitoring of the isomer composition be maximally accurate for compliance with a predetermined product specification. This monitoring must provide the composition as quickly as possible, so that the isomer system can be adjusted efficiently. Fast and maximally precise monitoring is particularly important since, due to the production technique, coupled products may be generated in the isocyanate isomer production.

The previously employed methods can meet these requirements only with significant limitations. In the offline gas-chromatographic examination, for example, the samples have to be taken and transported to the laboratory, where the sample is then prepared and subsequently analysed by gas chromatography.

An alternative to gas chromatography and titration, for quantitative analysis of the composition of substance mixtures, are the known spectroscopic methods from the prior art. These include, for example, near-infrared (NIR) spectroscopy, medium-infrared spectroscopy and Raman spectroscopy.

The analytical method of near-infrared (NIR) spectroscopy is a widespread technique, which is used both in the laboratory and in online operation. The combination of NIR spectroscopy with chemometric evaluation methods for special measurement tasks is likewise known per se from the prior art as described in, for example, DE 02139269, WO 97/41420, WO 98/29787, WO 99/31485, JP 11350368, WO 20002/0834, JP 2000146835, JP 2000298512, WO 2002/04394, WO 2002/12969, WO 95/31709, U.S. Pat. Nos. 5,707,870, 5,712,481, and WO 2000/68664.

Spectroscopic analysis techniques for determining the chemical properties of polymers and/or physical properties of polyurethane foams, both in the laboratory and in online operation, are known from "A review of process near infrared spectroscopy: 1980-1994" (J. Workman, J. Near Infrared Spectroscopy 1, 221-245 (1993)). The advantages of combining optical fibers and an NIR spectrometer, compared with using medium-infrared spectroscopy, are known from Khetty. See "In-line monitoring of polymeric processes" Antec '92, 2674-2676.

In order to use NIR spectroscopy in the field of quantitative determinations, the analytical method is frequently used in combination with chemometric evaluation methods. For example, it is customary to use the partial least-squares (PLS) method in this case, as can be found and described, for example, by Raphael Vieira in "In-line and In Situ Monitoring of Semi-Batch Emulsion Copolymerizations Using Near-Infrared Spectroscopy" J. Applied Polymer Science, Vol. 84, 2670-2682 (2002), or by T. Rohe in "Near Infrared (NIR) spectroscopy for in-line monitoring of polymer extrusion processes" Talanta 50 (1999) 283-290, or by C. Miller in "Chemometrics for on-line spectroscopy applications—theory and practice", J. Chemometrics 2000; 14:513-528 and in "Multivariate Analysis of Near-Infrared Spectra Using G-Programming Language" J. Chem. Inf. Comput. Sci. 2000, 40, 1093-1100.

The use of NIR techniques for special measurement tasks is furthermore known and described in, for example, WO 00/02035 (Determination of organic acids in organic polymers), U.S. Pat. No. 5,717,209 (Spectral analysis of hydrocarbons), U.S. Pat. No. 6,228,650; WO 99/31485 (Monitoring the separation of chemical components in an alkylation process with acid catalyst), U.S. Pat. No. 6,339,222; WO 00/68664 (Determination of ionic species in pulp liquor), and DE 10005130 A1 (Monitoring of polymer processes, determination of NCO in PU).

A review of the use of multivariate chemometric calibration models in analytical chemistry is also provided by "Multivariate Calibration", Jörg-Peter Conzen, 2001, ISBN 3-929431-13-0.

In the prior art, however, such spectroscopic methods are not used for isocyanate isomer mixtures.

SUMMARY OF THE INVENTION

It is therefore an object of the invention to provide an improved method for determining the isomer composition in an isocyanate isomer mixture, and an improved method for regulating or controlling an isocyanate isomer production system, and also an apparatus for the production of an isomer system.

The basis for the present invention is the surprising discovery that the absorption spectra of isocyanate isomer mixtures differ sufficiently from one another, even when there are only small concentration differences and/or individual isomers are kept at low levels, such that one can determine the isomer concentrations in an isocyanate isomer mixture on the basis of measuring the spectrum of the isocyanate isomer mixture, with the aid of a chemometric calibration model.

DETAILED DESCRIPTION OF THE INVENTION

Figure 1:
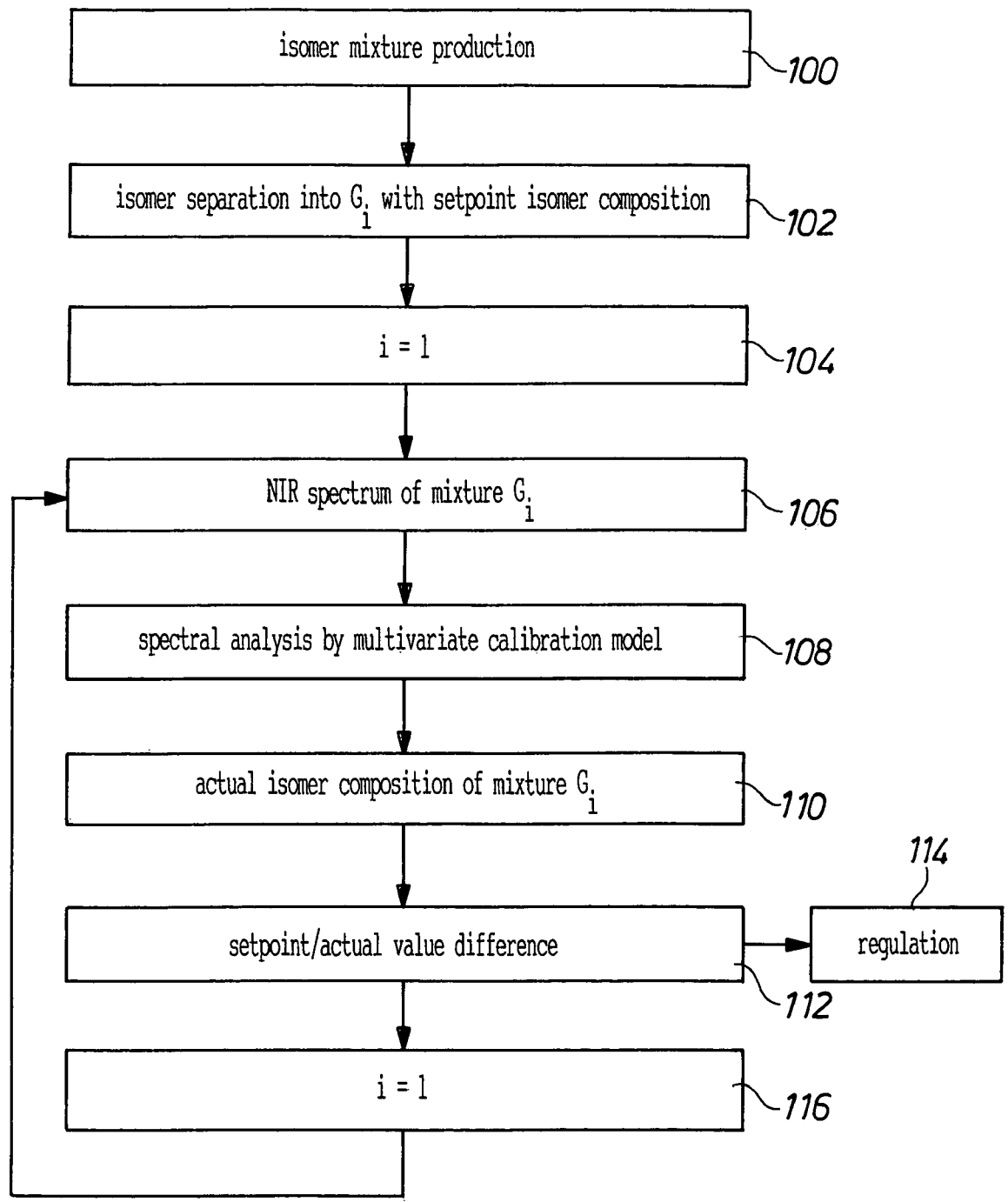
FIG. 1 is a flow chart of one embodiment of a method according to the invention for determining the isomer composition in various isomer mixtures.

In accordance with the method of the present invention, the isomer composition in an isocyanate isomer mixture is determined by (1) recording a spectrum of the isocyanate isomer mixture, for example by online analysis, possibly with an optical sensor by means of near-infrared (NIR) spectroscopy, medium-infrared spectroscopy or Raman spectroscopy, preferably NIR Spectroscopy. The process further comprises (2) entering the measured spectrum into a chemometric calibration model which has been set up previously for the mixture of these isocyanate isomers. The isomer concentrations in the isocyanate isomer mixture are obtained by evaluating the spectrum in the chemometric calibration model. In addition, the isomer production system can be adjusted accordingly by comparison of the actual concentrations of the isocyanate isomers as calculated in this manner with the specified setpoint isomer concentrations. The chemometric calibration model may, for example, be a multivariate model such as, for example, a partial least-squares algorithm.

A particular advantage of the present invention is that the concentration measurements can be carried out constantly, i.e. for example, at very small time intervals. This makes it possible to regulate or control the isomer production system within narrow ranges to yield an isocyanate isomer mixture with a setpoint isomer composition. In addition, the production of waste or a low product quality can be substantially avoided in this way.

Another advantage of the present invention is that the manual taking of samples and GC analysis are eliminated. This makes the present invention particularly advantageous in terms of occupational safety and environmental protection.

Another added advantage of the present invention is that the spectra can be recorded online and/or inline at one or more different positions within a complex system, without taking any samples. Such a complex system consists, for example, of a plurality of equipment components interconnected with one another, such as, for example, columns or crystallizers. This allows prompt and frequent gathering of information about the isomer concentrations. This information may be used for manual regulation or control of one or more of the parameters of the isomer production system, or alternatively, for continuous automatic regulation or control of the isomer production system.

In one embodiment of the present invention, a plurality of optical sensors for recording spectra may be arranged at different positions in an isomer production system in order to record the spectra of various isomer mixtures. These optical sensors may be connected, for example, via glass fibers, to a single spectrometer which functions in multiplex operation. This minimises the investment cost. Furthermore, sampling lines leading to an analysis instrument, which have an inherent risk of clogging due to crystallisation and the like, are eliminated due to this online analysis. This provides a particular advantage to the present invention, since such analysis lines are susceptible to problems and require extra handling of the resulting product-analysis substance flows.

Another advantage of the present invention is the possibility of automatic process management (e.g. control and/or regulation) on the basis of the isomer concentration information, with the concomitantly possible maintenance of an almost constant product quality with little energy outlay and with a high yield, as well as the consequent maximization of the isomer production system capacity.

Another specific advantage is the universal applicability of the present invention to a wide variety of isomer compositions in isocyanate production processes. For example, high measurement accuracies for determination of the isomer concentration can be achieved with the aid of the present invention, even when one or more of the isomers is present at very low concentrations, and also when the mixture concentrations are roughly of equal value. For example, concentration measurements of an isomer in an isomer mixture can be carried out with the aid of the present invention when the concentration of the isomer is between 0.01% and 99.99%. Some preferred applications for determination of the isomer composition in isocyanate production processes are set forth below. Preferred isomer compositions include:

a) 0-40% by weight of 2,6-TDI, with the balance being 2,4-TDI;
b) 0-3% by weight of 2,4'-MDI, 0-3% by weight of 2,2'-MDI, with the balance being 4,4'-MDI; and
c) 40% -70% by weight of 2,4'-MDI, 0% -3% by weight of 2,2'-MDI, with the balance being 4,4'-MDI.

DETAILED DESCRIPTION OF THE FIGURES

Reference will now be made to the various embodiments of the invention as illustrated in the figures and explained in more detail below.

FIG. 1 shows a flow chart of one embodiment of a method according to the invention for determining the isomer composition of various isomer mixtures. In FIG. 1, a raw isomer mixture is produced in a production system in step 100. The mixture is, for example, a raw MDI mixture which may consist of three MDI isomers, or a raw TDI mixture which may consists of up to four TDI isomers. In step 102, one or more isomer mixtures $G_i$ which respectively have a particular setpoint isomer composition are produced by, for example, isomer separation from the raw isomer mixture which was produced in step 100. This is done in, for example, an isomer separation system by means of, for example, distillation or crystallisation. Instead of an isomer separation system, an isomer mixing system may also be employed.

The index i is initialised in step 104. The spectrum of the isomer mixture $G_i$ is measured online at the output of the isomer production system in step 106. This is done, for example, by an online NIR spectral measurement. The measurement is carried out, for example, using an optical sensor which is connected to an NIR spectrometer by means of a glass-fiber cable.

The measured NIR spectrum is spectrally analysed with the aid of a chemometric calibration model in step 108. This provides the actual isomer composition of the isomer mixture $G_i$ in step 110. The difference between the setpoint isomer composition and actual values of the isomer composition mixture $G_i$ is calculated in step 112. On the basis of this difference in value, adjustment of the isomer production system is carried out in step 114. The index i is incremented in step 116, and the next spectrum is measured in step 106. This procedure is repeated until the actual isomer composition has been determined once for all the mixtures $G_i$. The index i is then reset, so that the actual isomer compositions of all the mixtures $G_i$ are determined continuously within relatively short time intervals, for example, over a few minutes, and corresponding adjustments can be carried out promptly.

Figure 2:
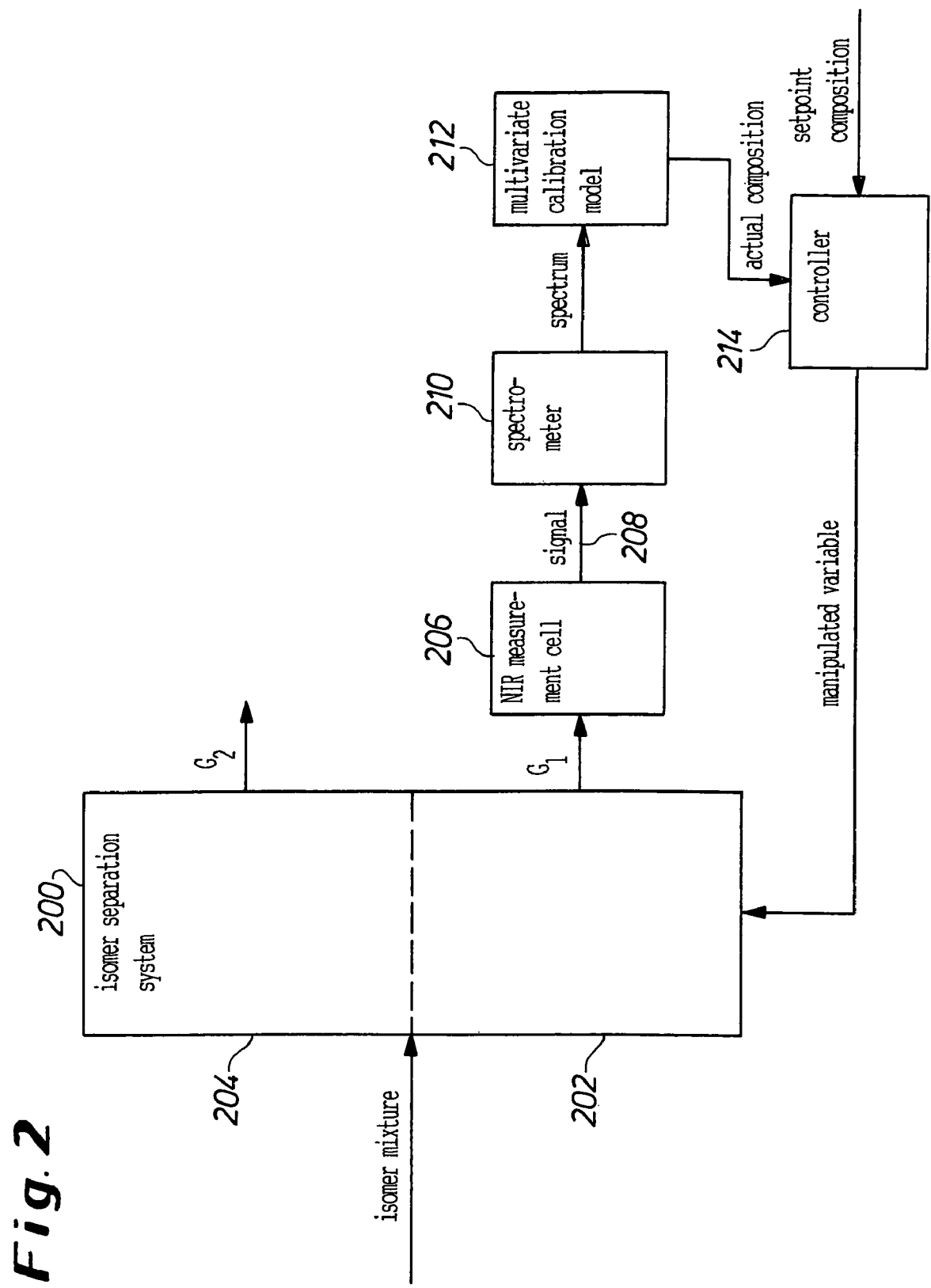
FIG. 2 is a block diagram of one type of an isomer separation system with a means for regulating or controlling the isomer separation system.

FIG. 2 is a block diagram of one type of an isomer production system with a means of regulating or controlling the isomer production system in accordance with the present invention.

In particular, FIG. 2 shows an isomer production system 200, specifically an isomer separation system, which separates the incoming raw isomer mixture entering the production system 200, into two isomer mixtures $G_1$ and $G_2$. Each isomer mixture $G_1$ and $G_2$ has a defined isomer concentration. Isomer mixture $G_1$ is obtained in the bottom region 202 of the distillative isomer separation system 200, and isomer mixture $G_2$ is obtained in the head region 204 of the isomer separation system 200.

An optical measurement cell 206 is arranged at least at the output of the bottom region 202 of the isomer separation system 200. The measurement cell 206 contains an NIR sensor and may, for example, be designed with the "Pressure-tight process window" claimed in WO 00/58711, believed to correspond to U.S. application Ser. No. 09/937,409 filed on Sep. 24, 2001, the disclosure of which is herein incorporated by reference. Optical measurement cell 206 provides analytical information from the bottom region 202 of the isomer separation system 200 about isomer mixture $G_1$. The measurement cell 206 is preferably connected to a spectrometer 210 via an optical fiber 208 or other suitable means. The spectrometer 210 provides a spectrum of isomer mixture $G_1$, which is entered into a chemometric calibration model 212. The chemometric calibration model 212 may be formed using a separate evaluation unit such as, for example, a commercially available PC. Alternatively, the spectrometer 210 itself may contain such an evaluation unit for the spectrum.

As a result of the analysis of the measured spectrum, the chemometric calibration model 212 provides the actual composition of the isomer mixture $G_1$. This actual composition is entered into a controller 214, together with the setpoint isomer composition of the isomer mixture $G_1$. The difference between the actual isomer composition of $G_1$ and the setpoint isomer composition of $G_1$ is calculated. From this difference, the controller 214 determines a manipulated variable for adjusting the isomer production system 200.

It is not absolutely necessary to measure the spectrum of the mixture $G_2$ in the embodiment of FIG. 2, since the isomer concentrations in the mixture $G_2$ are readily determined from the known concentrations in the raw isomer mixture entering the isomer separation system 200 and the actual composition of the mixture $G_1$ in the bottom region 202 of the isomer separation system 200.

In an optional embodiment (not shown in FIG. 2), there may be other sensors 206, which are in turn connected to the spectrometer 210 via suitable means such as other optical fibers 208. These other sensors 206 may be arranged at various positions within the isomer separation system 200, such as, for example, at various columns (also not shown) within the separation system 200. The spectrometer 210 is then operated in multiplex, as are the chemometric calibration model 212 and the controller 214. These other sensors permit the measurement of isomer mixture $G_1$ at various positions in the isomer separation system 200, and the generation of corresponding spectra. In this embodiment, it is preferred that these sensors are located at positions such that measurements are provided for the inputs, inside the separation equipment, and/or in an isolated fraction.

The raw isomer mixture is, for example, a raw monomer mixture of MDI which consists of the three isomers 2,4'-MDI, 2,2'-MDI and 4,4'-MDI.

The controller 214 may be formed by a process management system of the isomer separation system 200. Alternatively, it is also possible to display the measurement results, for example on a display unit of a control panel (not shown) of the isomer separation system 200, so that the isomer separation system 200 can be adjusted manually.

Figure 3:
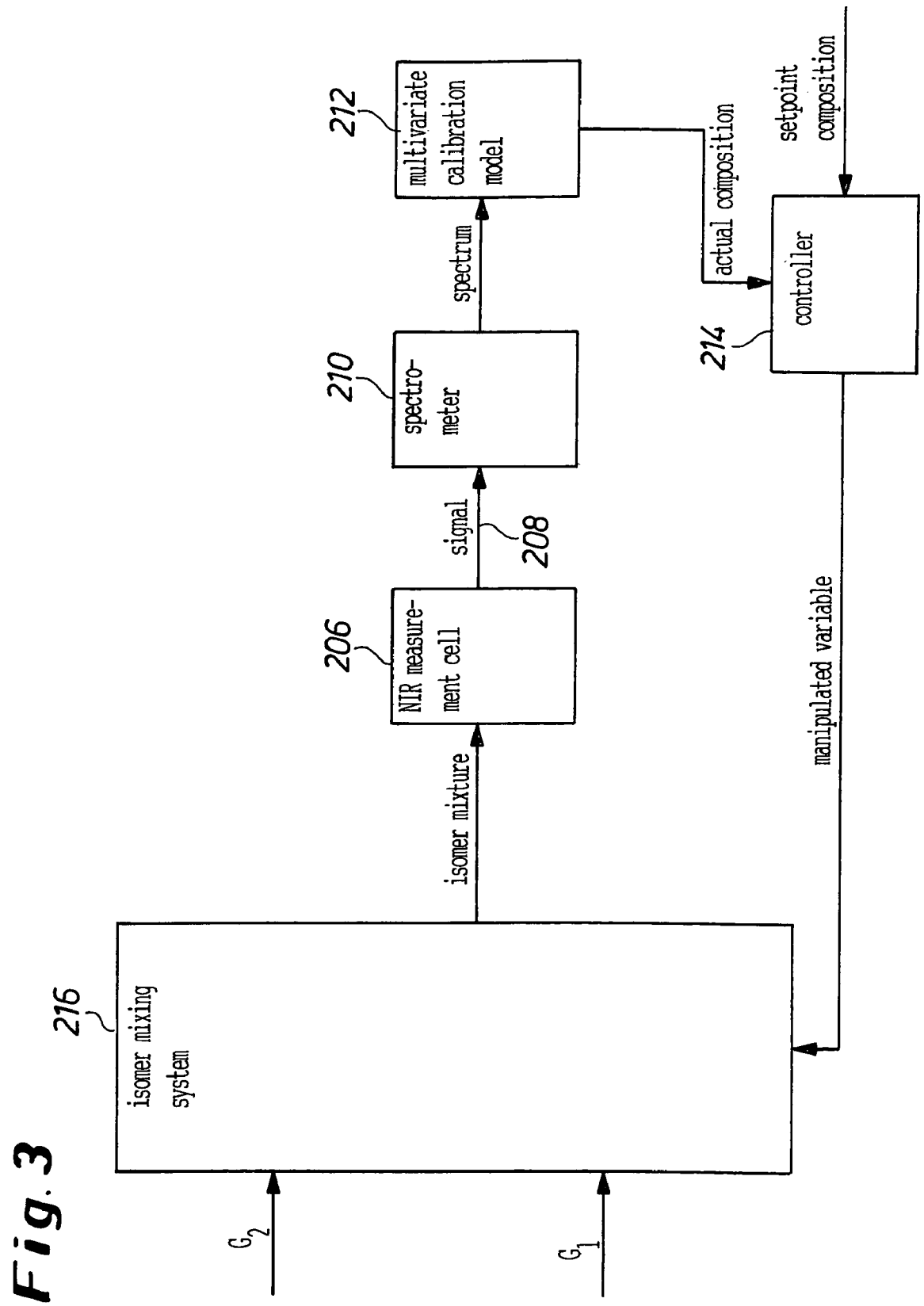
FIG. 3 is a block diagram of one type of an isomer mixing system with a means for regulating or controlling the isomer mixing system.

FIG. 3 is a block diagram of another type of an isomer production system, specifically an isomer mixing system, with a suitable means for regulating or controlling the isomer production system.

FIG. 3 illustrates an isomer mixing system 216 with one possible embodiment of the means for regulation of the system in accordance with the present invention. In FIG. 3, the elements of the isomer mixing system 216 which correspond to the elements of the isomer separation system 200 of FIG. 2 are labelled with the same reference numbers as in FIG. 2. The isomer mixing system 216 is used for the production of an isomer mixture, having a particular setpoint isomer composition, from a blend of various isomers. A spectrum of the isomer mixture produced in the isomer mixing system 216 is determined by means of the measurement cell 206, which is connected to a spectrometer 210 via an optical fiber 208 or other suitable means. This spectrum is entered into a chemometric multivariate calibration model 212. As a result of the analysis of the measured spectrum, the chemometric calibration model 212 provides the actual isomer composition of the isomer mixture in isomer mixing system 216. This actual isomer composition is entered into a controller 214, together with the setpoint isomer composition of the isomer mixture. From the calculated difference between the actual isomer composition and the setpoint isomer composition, the controller 214 determines a manipulated variable which is used to adjust or regulate the isomer mixing system 216.

Figure 4:
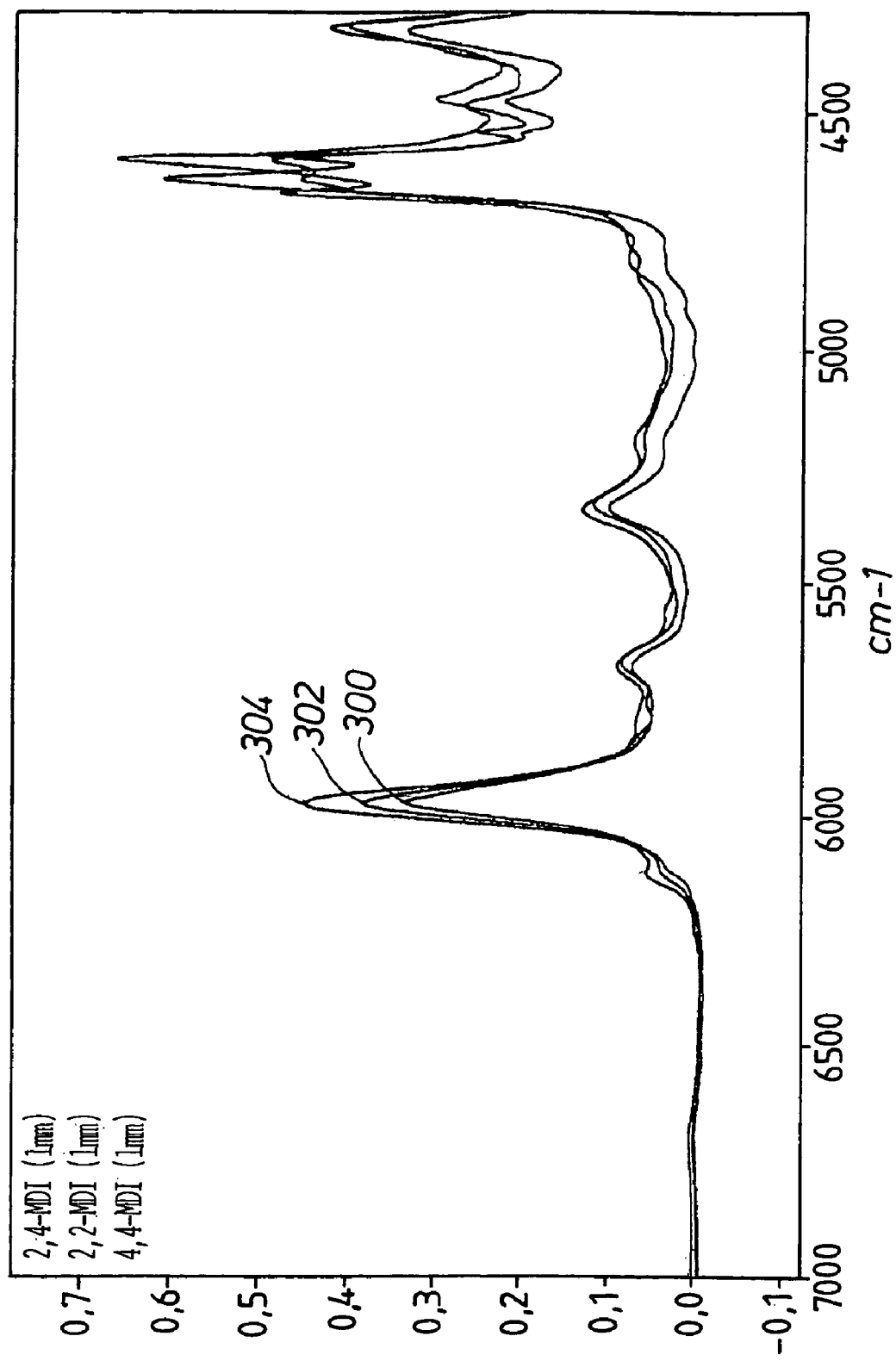
FIG. 4 shows the various spectra of MDI isomers.

In order to produce the isomer mixture, two or more pure isomers or isomer mixtures $g_1$, $g_2$, ... are delivered to the isomer mixing system 216. These may, for example, be pure TDI isomers and/or TDI isomer mixtures, or, for example, pure MDI isomers and/or MDI isomer mixture, etc. In order to monitor the compositions of the isomers or isomer mixtures $g_1$, $g_2$, ..., one or more other measurement cells 206 which are likewise connected to the spectrometer 210 may respectively be arranged at the corresponding inputs of the isomer mixing system in order to monitor the actual compositions of the initial substances $g_1$, $g_2$, .... FIG. 4 illustrates the various spectra of MDI isomers. In particular, FIG. 4 hows examples of the corresponding spectra for the different isomers of MDI. Specifically, the spectrum 300 represents pure 4,4'-MDI, the spectrum 302 represents pure 2,4'-MDI and the spectrum 304 represents pure 2,2'-MDI. As seen in FIG. 4, these spectrum 300, 302, 304 are similar.

Figure 5:
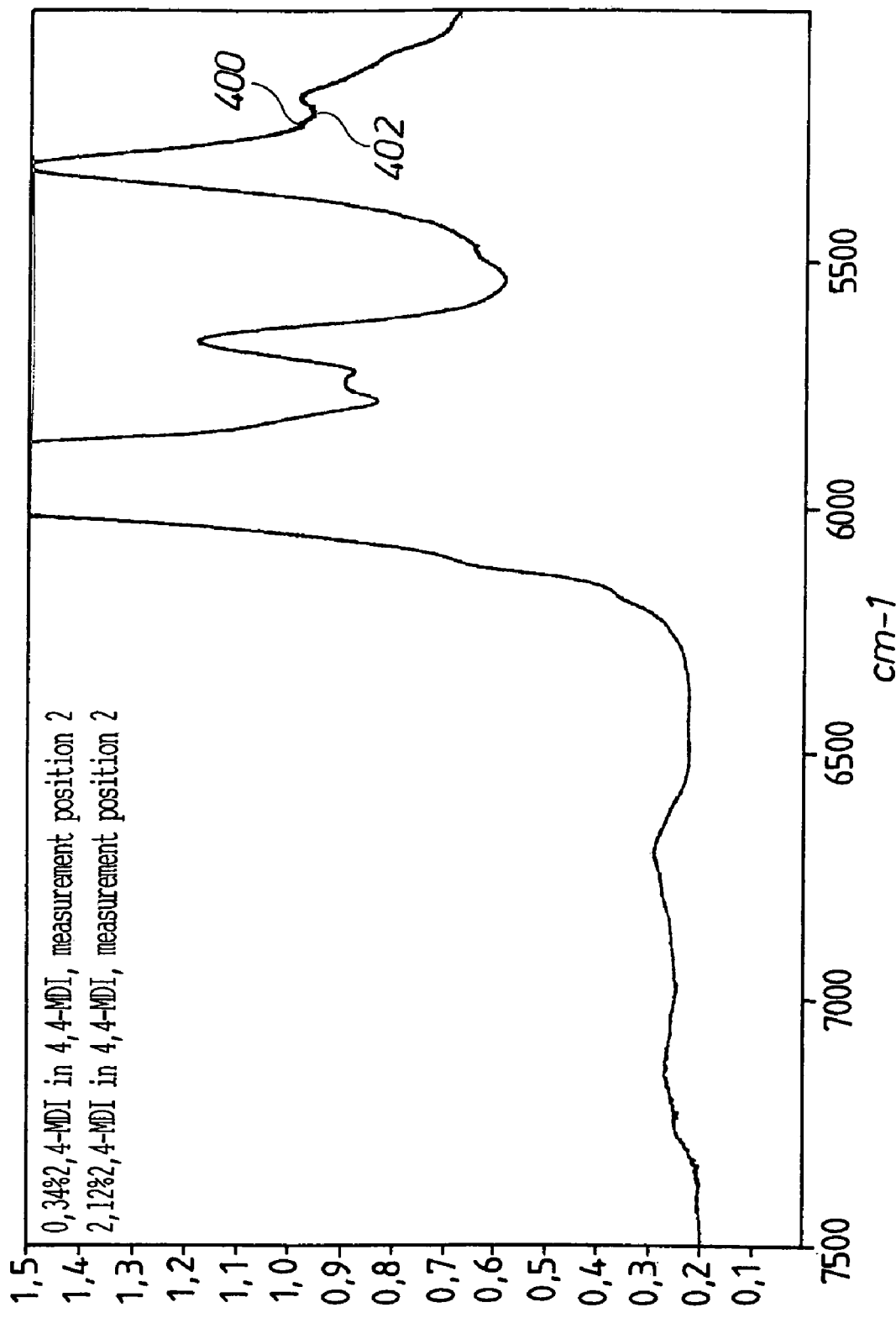
FIG. 5 shows the spectra of two different MDI isomer mixtures.

FIG. 5 illustrates the spectra of two different MDI isomer mixtures. More specifically, the shows the spectrum 400 represents an isomer mixture comprising 0.34% of 2,4'-MDI in 4,4'-MDI. A mixture such as this can be obtained, for example, as a mixture $G_1$ from the bottom region 202 of the isomer separation system 200 (cf. FIG. 1). FIG. 5 also shows the spectrum 402 of an isomer mixture comprising 2.12% of 2,4'-MDI in 4,4'-MDI. As can be seen from FIG. 4, the spectra of these isomer mixtures are almost identical.

Figure 6:
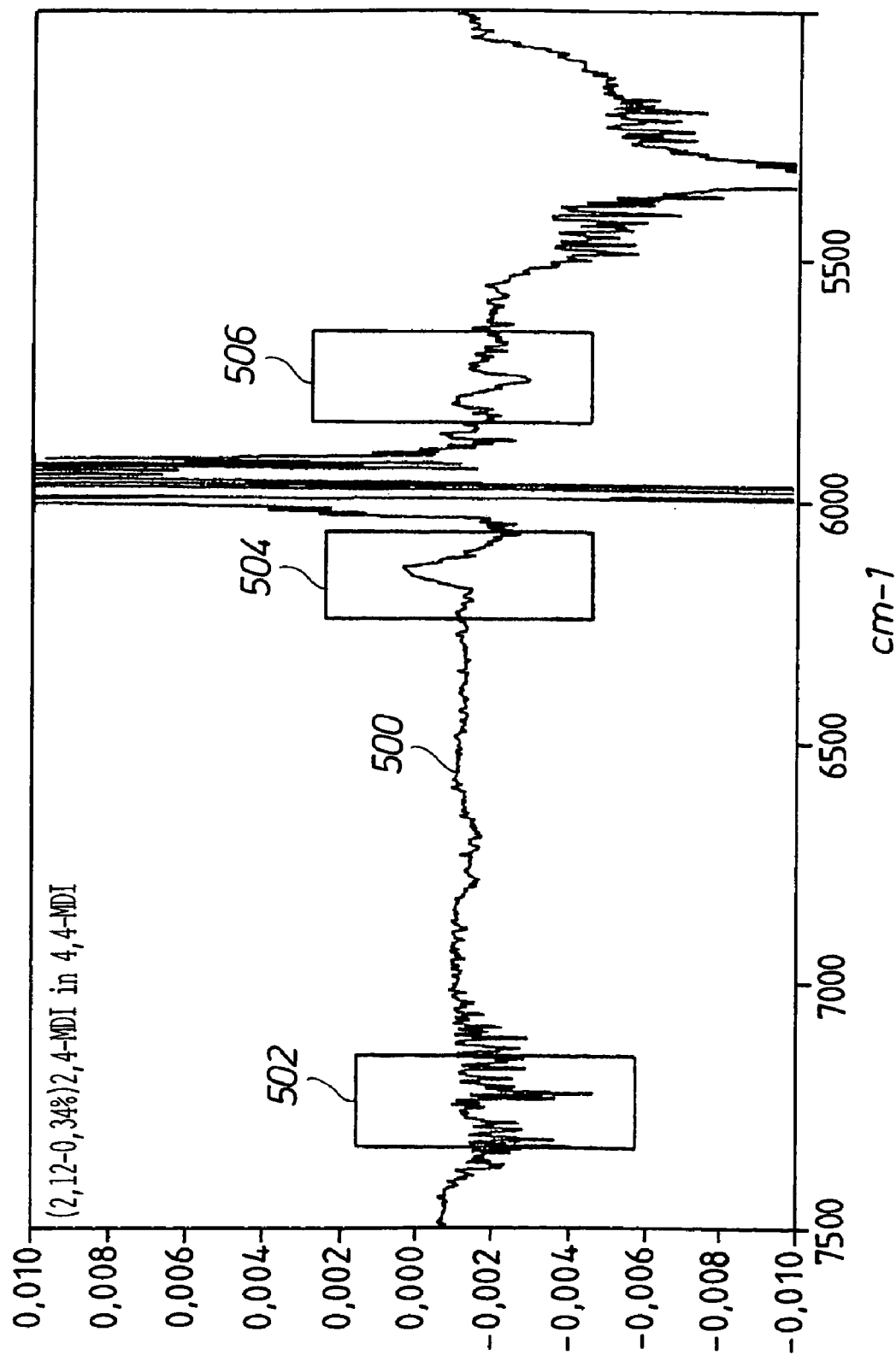
FIG. 6 shows the differential spectrum of the spectra as shown in FIG. 5.

FIG. 6 shows the differential spectrum of the spectra set forth in FIG. 5. Specifically, FIG. 6 shows the differential spectrum of the spectra 402 and 400 in FIG. 5. It is preferred that only the frequency ranges 502 and/or 504 and/or 506 shown in FIG. 6 are used for evaluation in the multivariate calibration model 212 (cf. FIG. 2). Preferred frequency ranges for evaluation of the spectrum include, for example, the frequency ranges 5000 to 7000 $cm^{-1}$, and preferably 6250 to 6080 $cm^{-1}$ or 5840 to 5650 $cm^{-1}$. Isomer concentrations in an isomer mixture which are in the range, for example, from 0.01% to 99.99%, can be determined in this manner with an accuracy of better than 0.1% in absolute. terms. Therefore, controller intervention can take place even with a setpoint difference of only 0.1%. The setpoint difference is the difference between the setpoint isomer composition and the actual isomer composition as measured. This ensures an almost constant product quality at any time, and particularly when the regulation or control of the isomer production system is fully automatic.

The absorption spectra are processed either as original spectra or as first-, second- or higher-derivative spectra. It is preferred that the first-derivative spectra are processed.

Figure 7:
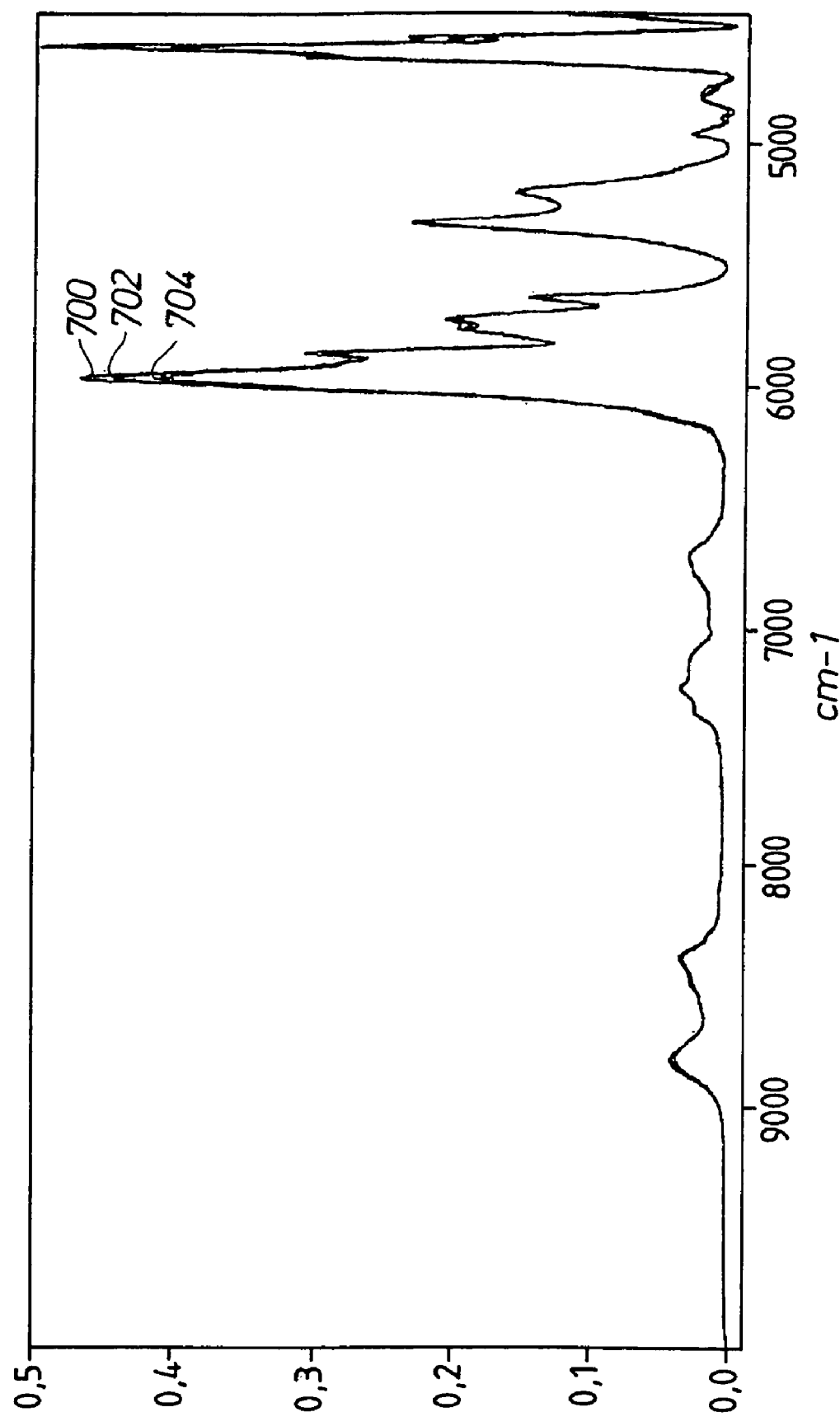
FIG. 7 shows the various spectra of TDI isomers.

FIG. 7 illustrates various spectra of TDI isomers,

In particular, FIG. 7 shows the spectra which correspond to various mixtures of 2,4-TDI and 2,6-TDI. The spectrum 700 is obtained for an isomer mixture comprising 67% of 2,4-TDI with the balance being 2,6-TDI; the spectrum 702 is obtained for an isomer mixture comprising 81% of 2,4-TDI with the balance being 2,6-TDI; the spectrum 704 is obtained for an isomer mixture having a concentration ≧99.5% of 2,4-TDI with the balance being 2,6-TDI. As seen in FIG. 7, the spectra 700, 702 and 704 are very similar. The present invention nevertheless makes it possible for even small concentration differences to be accurately determined.

Figure 8:
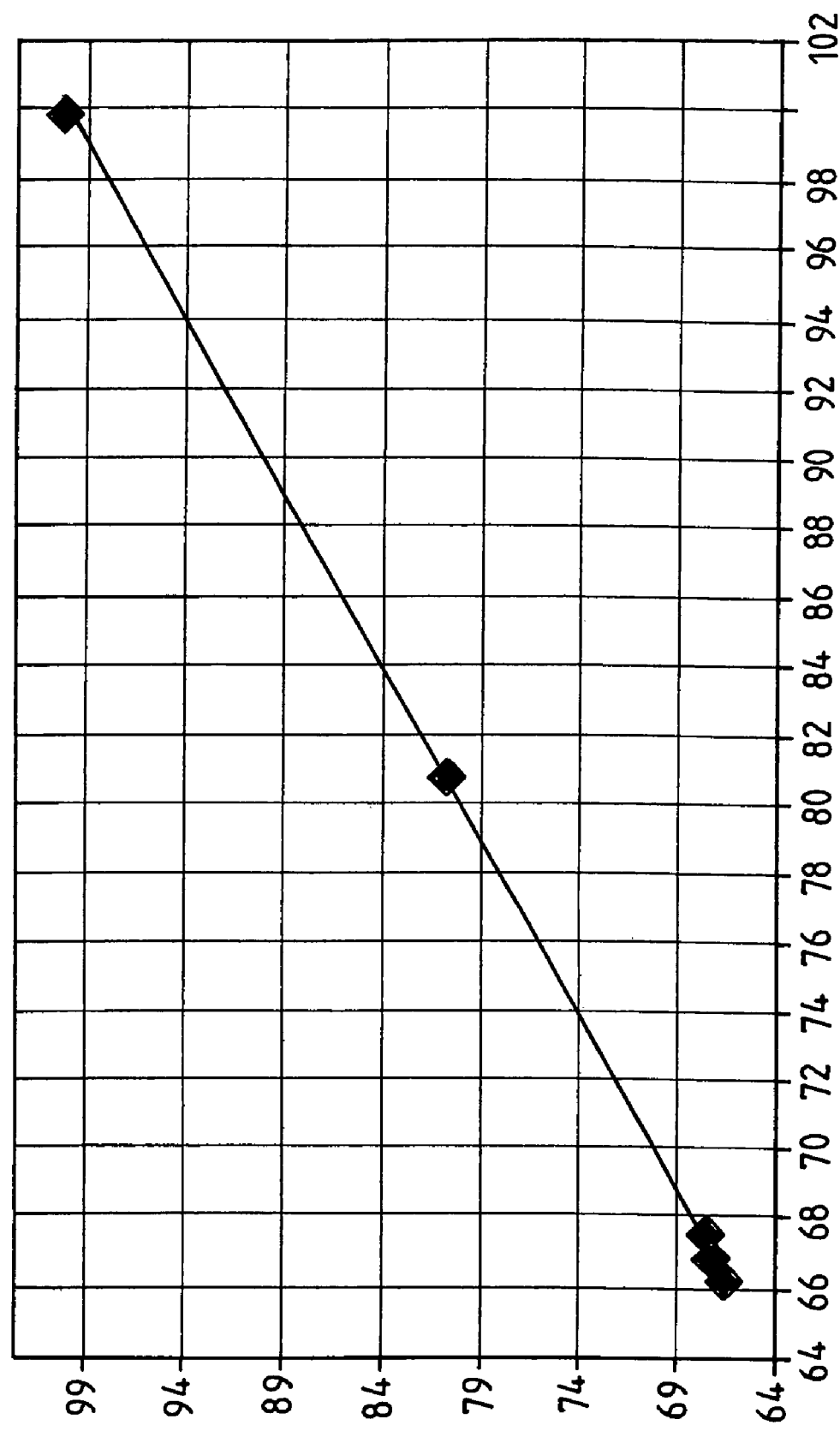
FIG. 8 shows a calibration curve for the determination of 2,4-TDI in 2,6-TDI.

FIG. 8 shows the calibration curve for determination of 2,4-TDI in 2,6-TDI. It can be seen from this that highly accurate quantitative analysis is possible, in spite of the similarity of the spectra as seen in FIG. 7. Preferred frequency ranges for evaluation of the spectrum are the frequency ranges 4500 to 9000 $cm^{-1}$, and preferably 5610 to 6220 $cm^{-1}$ and 5240 to 5840 $cm^{-1}$.

| List of references used in the figures: | |
|---|---|
| isomer separation system | 200 |
| bottom region | 202 |
| head region | 204 |
| measurement cell | 206 |
| optical fiber | 208 |
| spectra | 210 |
| chemometric calibration model | 212 |
| controller/regulator | 214 |
| isomer mixing system | 216 |
| 4,4'-MDI spectrum | 300 |
| 2,4'-MDI spectrum | 302 |
| 2,2'-MDI spectrum | 304 |
| spectrum | 400 |
| spectrum | 402 |
| spectrum | 500 |
| frequency range | 502 |
| frequency range | 504 |
| frequency range | 506 |
| spectrum | 700 |
| spectrum | 702 |
| spectrum | 704 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method to determine the isomer composition of an isocyanate isomer mixture comprising a mixture of isomers of methylene diphenyl diisocyanate, comprising:
   (1) recording a spectrum of the isocyanate isomer mixture, and (2) evaluating the spectrum in a frequency range selected from the group consisting of 6250 to 6080 cm$^{-1}$, 5840 to 5650 cm$^{-1}$ and a combination of the frequency ranges of 6250 to 6080 cm$^{-1}$ and 5840 to 5650 cm$^{-1}$, by a chemometric calibration model, thereby determining the actual isomer composition of the isocyanate isomer mixture.

2. The method of claim 1, wherein the spectrum is a near-infrared (NIR) spectrum, a medium-infrared spectrum or a Raman spectrum.

3. The method of claim 1 wherein the recording of the spectrum occurs online or inline, without taking samples.

4. The method of claim 1, additionally comprising
(3) adjusting the composition of the isocyanate isomer mixture based on the actual isomer composition of the isocyanate isomer mixture as calculated by the chemometric calibration model.

5. The method of claim 4, wherein (3) adjusting of the composition is performed manually or automatically.

6. The method of claim 1, wherein the isomer concentrations present in the isocyanate isomer mixture are in the range from 0.01% to 99.99%.

7. The method of claim 1 wherein the chemometric calibration model in (2) comprises a partial least-squares method.

8. A method for regulating an isocyanate isomer production system, comprising:
(1) recording a spectrum of an isocyanate isomer mixture comprising a mixture of isomers of methylene diphenyl diisocyanate,
(2) evaluating the spectrum in a frequency range selected from the group consisting of 6250 to 6080 cm$^{-1}$ 5840 to 5650 cm$^{-1}$ and a combination of the frequency ranges of 6250 to 6080 cm$^{-1}$ and 5840 to 5650 cm$^{-1}$, by a chemometric calibration model to determine the actual isomer composition of the isocyanate isomer mixture,
(3) calculating the difference between the setpoint isomer composition and the actual isomer composition, and
(4) adjusting one or more process parameters of the isocyanate isomer production system in accordance with the difference calculated in (3),
thereby enabling the production of an isocyanate isomer mixture with a setpoint isomer composition.

9. The method of claim 8, wherein the isocyanate isomer mixture in (1) is formed by distillation or crystallisation in the isocyanate isomer production system.

10. The method of claim 8, wherein recording of the spectrum is by means of one or more optical sensors.

11. The method of claim 8, wherein recording of the spectrum is by means of near-infrared (NIR) spectroscopy, medium-infrared spectroscopy or Raman spectroscopy.

12. The method of claim 8, wherein the recording of the spectrum occurs online or inline.

* * * * *

UNITED STATES PATENT AND TRADEMARK OFFICE
CERTIFICATE OF CORRECTION

PATENT NO. : 7,662,634 B2  Page 1 of 1
APPLICATION NO. : 10/845727
DATED : February 16, 2010
INVENTOR(S) : Mahrenholtz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1256 days.

Signed and Sealed this

Thirtieth Day of November, 2010

David J. Kappos
*Director of the United States Patent and Trademark Office*